United States Patent [19]
Walters

[11] Patent Number: 5,797,955
[45] Date of Patent: *Aug. 25, 1998

[54] PRESSURE APPLICATION UNIT FOR POSITIONING VERTEBRA

[76] Inventor: David J. Walters, P.O. Box 637, Erwin, Tenn. 37650

[*] Notice: The term of this patent shall not extend beyond the expiration date of Pat. No. 5,792,085.

[21] Appl. No.: 870,880

[22] Filed: Jun. 9, 1997

Related U.S. Application Data

[63] Continuation-in-part of Ser. No. 661,822, Jun. 11, 1996.
[51] Int. Cl.⁶ ................................. A61B 17/00; A61F 5/00
[52] U.S. Cl. ........................... 606/204; 602/19; 606/201
[58] Field of Search ................................. 606/201–204, 606/204.15; 602/1, 5, 19, 20, 23, 32, 36, 60, 61, 74, 67

[56] References Cited

U.S. PATENT DOCUMENTS

| | | | |
|---|---|---|---|
| 5,445,647 | 8/1995 | Choy | 606/204 |
| 5,470,304 | 11/1995 | Decanto | 606/204 |

FOREIGN PATENT DOCUMENTS

| | | | |
|---|---|---|---|
| 3819859 | 6/1988 | Germany | 606/204 |

*Primary Examiner*—Glenn K. Dawson

[57] ABSTRACT

A device for applying external pressure to one or more vertebra for repositioning the same and/or maintaining the position thereof in the spinal column, or for forcing and maintaining segments of a broken vertebra in healing contact with each other. The device has an upper body vest adapted to substantially surround the upper body of a patient in a snug manner whereby the vest is substantially immovable relative to the upper body. The vest has front and back sections provided with cooperating elements of an attachment mechanism such as Velcro or belt and adjustable buckle, for clamping the sections to the upper body. The back section has a pressure applicator unit extending substantially the length of the back section for applying external pressure, generally posteriorly to one or more vertebra. The applicator having a plunger or thrust mechanism such as a screw with a cushion on the end thereof and mounted for controlled, reciprocable movement in a direction toward the spine for applying the external pressure in a controlled manner to one or more vertebra areas.

12 Claims, 8 Drawing Sheets

PRESSURE APPLICATION UNIT FOR POSITIONING VERTEBRA

This application is a continuation-in-part of applicants pending Ser. No. 08/661,822, filed Jun. 11, 1996, of same title.

BACKGROUND OF THE INVENTION

1. Field of the Invention

This invention relates to a back treatment device and more particularly to a device which can apply force and pressure to selected portions of the human spine i.e., specific vertebra or segments thereof such as the spinous, mammillary, superior and inferior articular, and transverse processes, without effecting pressure-caused discomfort to other portions of the patients body.

2. Description of the Prior Art

Most individuals experience back problems at some point in their lives, either thru normal wear and tear or thru accident. These problems often are centered about displacement of one or more vertebra thru injury to spinal discs, or ligament damage, e.g., to the supraspinous, posterior longitudinal, ligamentum flavum, interspinal, or anterior longitudinal ligaments, or back muscle tear, or thru actual vertebra fracture whereby a segment of the vertebrae is in a fractured and dislocated condition. Various treatment mechanisms and methods are utilized to treat such back ailments or injuries and associated trauma and often include devices which strap to the patient for applying force and pressure to specific localized areas of the spine.

It is of course, often advantageous to apply such force to specific portions of the spine for lengthy rehabilitative periods and with varying degrees of pressure at different times during the healing period.

Many mechanisms have been developed for applying such pressures as indicated by U.S. Pat. Nos. 5,086,757; 3,709,216; 5,507,135; 2,593,624; 1,424,884; 5,135,471; 2,180,775; 3,926,182; 2,835,247; 5,127,897, the disclosures of which with regard to utility, construction materials and specific structures or the like are hereby incorporated herein in their entirety.

In the use of these prior mechanisms very noticeable problems arise such as limited adjustability, if any, of the pressure point, particularly with respect to angular positioning about or in the plane of the spinal axis. Also, these mechanisms are typically very complex and employ straps or the like girding the body at spaced locations for generating the necessary opposing forces to the pressure applicator. Such straps cause discomfort to the patient, especially where the application of pressure is over a period of more than a few minutes and the pressure is of a significant degree.

OBJECTS OF THE INVENTION

Accordingly, it is a principal object of the present invention to provide a therapeutic pressure applicator device adapted to be worn by the patient and which is comfortable over long periods of time and which can apply any degree of pressure, in a wide range of axial and lateral selected angles, to selected vertebra areas of the spine.

The above and further objects hereinafter becoming evident have been attained in accordance with the present invention thru the discovery of structure for a pressure applicator device which, in its broad context, is defined as a device for applying external pressure to one or more vertebra for repositioning the same and/or maintaining the position thereof in the spinal column and with respect to the spinal axis, or for forcing and maintaining segments of a fractured vertebra in healing contact with each other, said device comprising an upper body vest means adapted to substantially surround the upper body of a patient in a snug manner whereby said vest means is substantially immovable relative to said upper body, said vest means having front and back sections provided with cooperating segments of attachment means for clamping said sections to said upper body, said back section having a spinal plane, pressure applicator means on said back section extending substantially the length of said back section for applying external pressure, generally posteriorly to one or more vertebra, said applicator means having thrust means mounted for controlled, reciprocable movement generally normal to said spinal axis for applying said external pressure in a controlled manner to one or more vertebra.

In certain preferred embodiments:

(a) said plunger means is mounted for limiting, universal type motion whereby pressure can be directed in a wide range of angles against the spine;

(b) said vest means comprises sections which are custom formed to fit a particular patients body; and (c) said cooperating elements of said attachment means comprises quick release hook and loop (Velcro) segments.

BRIEF DESCRIPTION OF THE DRAWINGS

The invention will be further understood from the following description and drawings of certain preferred embodiments wherein portions of the structure are shown enlarged for purposes of clarity and wherein the figures are not drawn to the same scale.

DETAILED DESCRIPTION OF THE DRAWINGS

Figure 1:
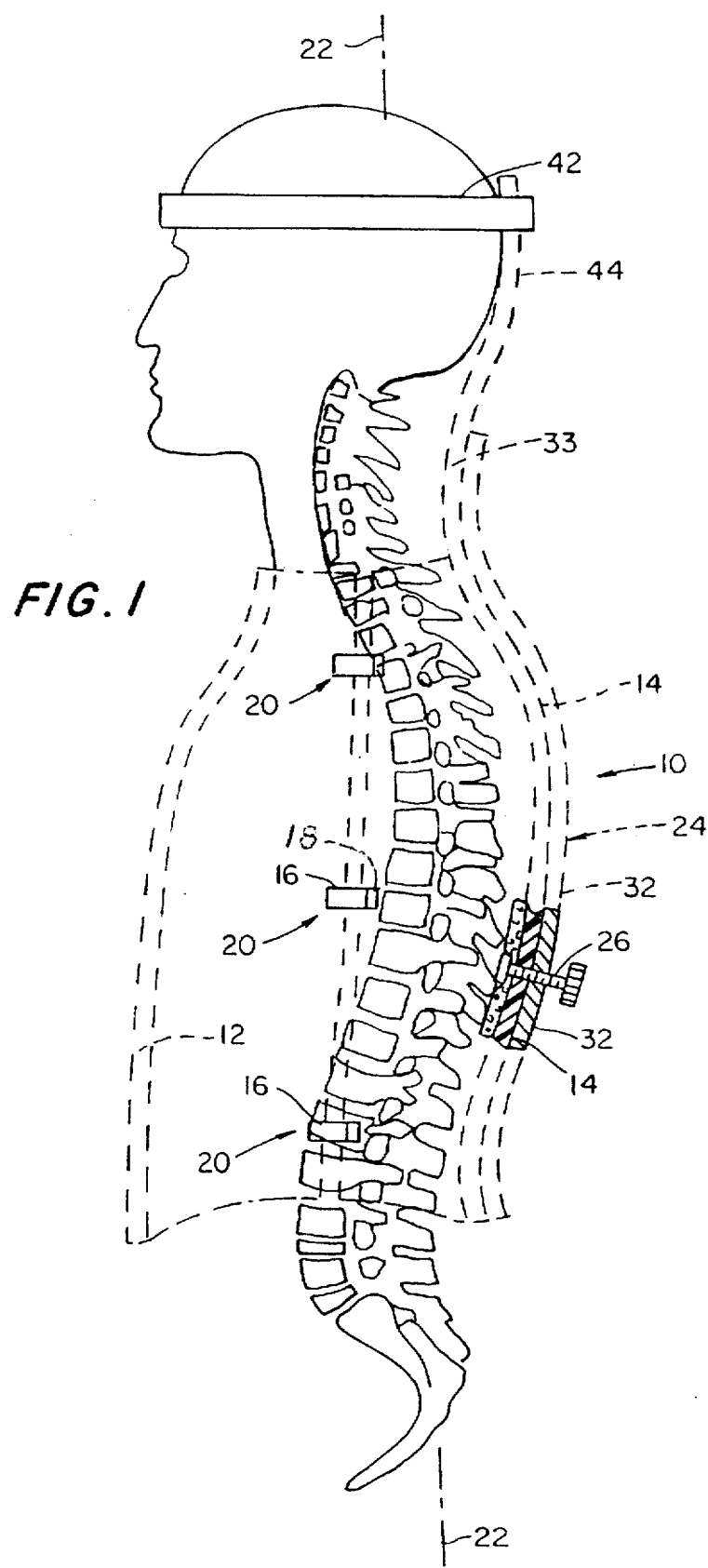
FIG. 1 is a side view of a patient wearing a simplified embodiment of the present device with portions thereof shown in phantom line.

The invention will be further understood from the following description with particular reference to the claims hereof, wherein the present device comprises an upper body vest means generally designated 10 dimensioned and adapted to substantially surround the upper body of a patient in a snug manner from approximately the waist to the head whereby said vest means is substantially immovable relative to said upper body, said vest means having front 12 and back 14 sections provided with cooperating segments 16, 18 of attachment means generally designated 20 for clamping said sections to said upper body, said back section 14 having an approximate spinal axis generally designated 22, pressure applicator means generally designated 24 on said back section extending substantially the length of said back section for applying external pressure, generally posteriorly to one or more vertebra 27 along the length of the spine 25, said applicator means having thrust means generally designated 26 mounted for controlled, reciprocable movement generally normal to said spinal axis for applying said external pressure in a controlled manner to one or more vertebra.

Each vest section may be comprised of any material which can afford both rigidity and comfort and preferably has a rigid or at least semi-rigid backing means 28 such as a vinyl, polyurethane, polyolefin, polyester, polyamide, plaster or paris, or the like, preferably in molded form. In this regard, the backing means may be form-fitted during its molding or forming to precisely fit a patients body contours for maximizing patient comfort and performance of the vest means.

In a most preferred embodiment, a cushion means 30 is adhered or otherwise affixed to the inside of the vest sections to allow the sections to be latched tightly to the body whereby the cushion means acts to distribute the reactive force to the pressure generated by the applicator means over large areas of the body, thus avoiding localized pressure points and their attendant discomfort. The cushion means preferably is of sponge type plastic material such as polyurethane or vinyl foam or the like, but also may be of thick, felt-like fabric or similar construction.

Figure 2:
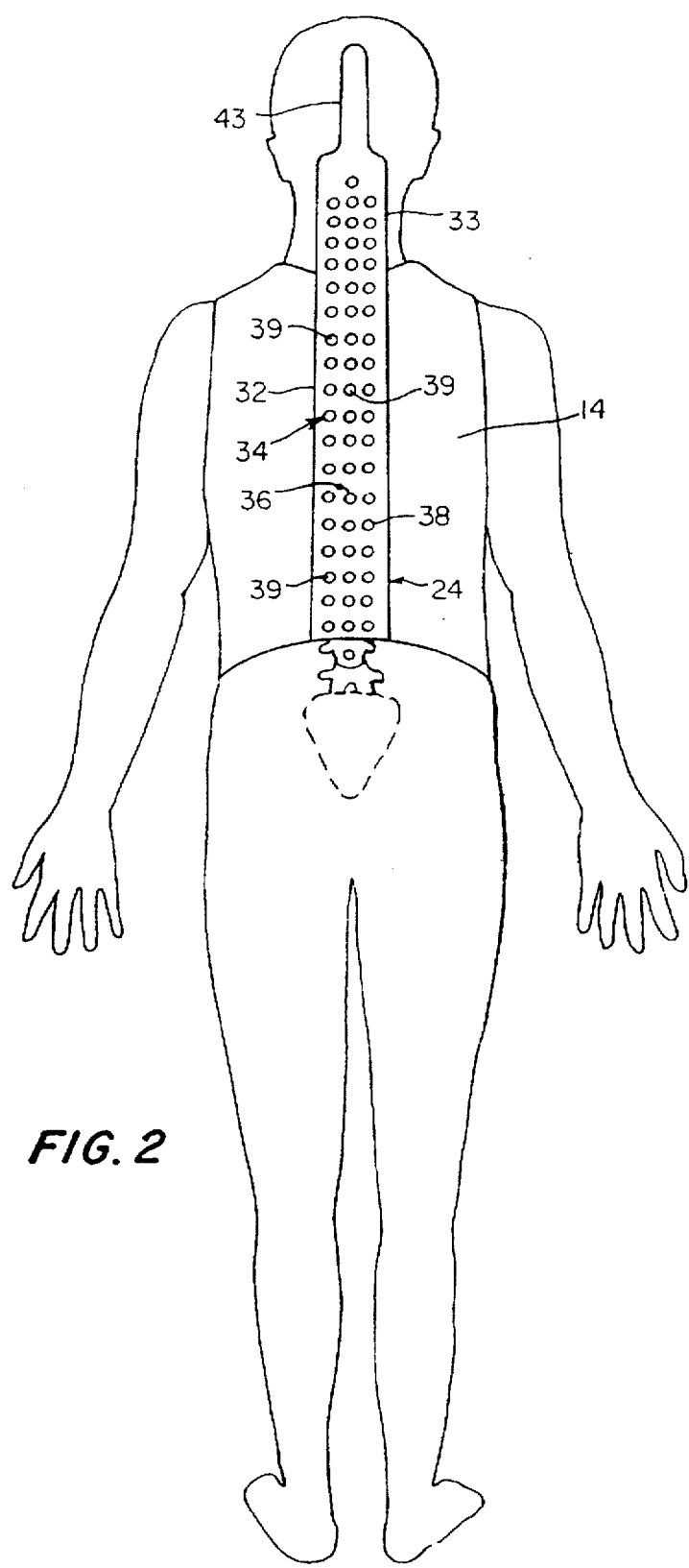
FIG. 2 is a rear view of the patient and device of FIG. 1.
Figure 3:
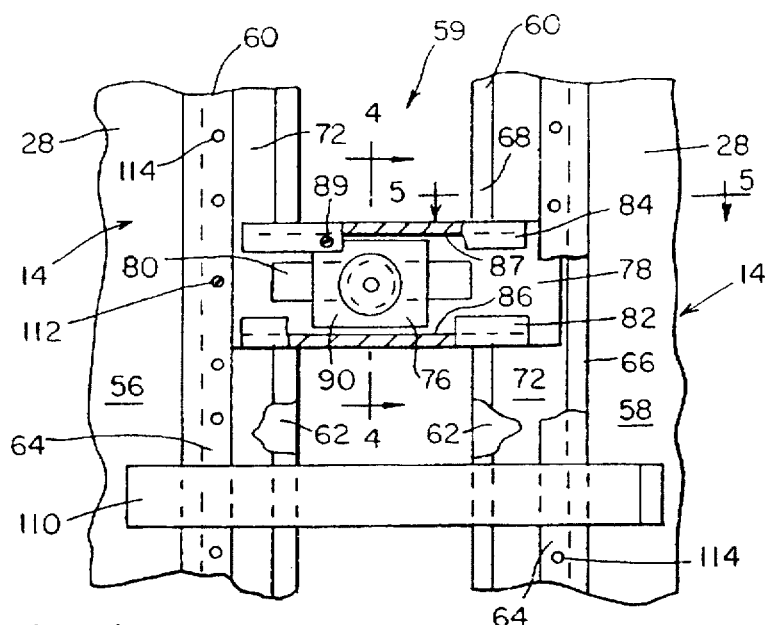
FIG. 3 is a rear elevational view of a preferred embodiment of the pressure applicator means with portions of the structure broken away for clarity.
Figure 4:
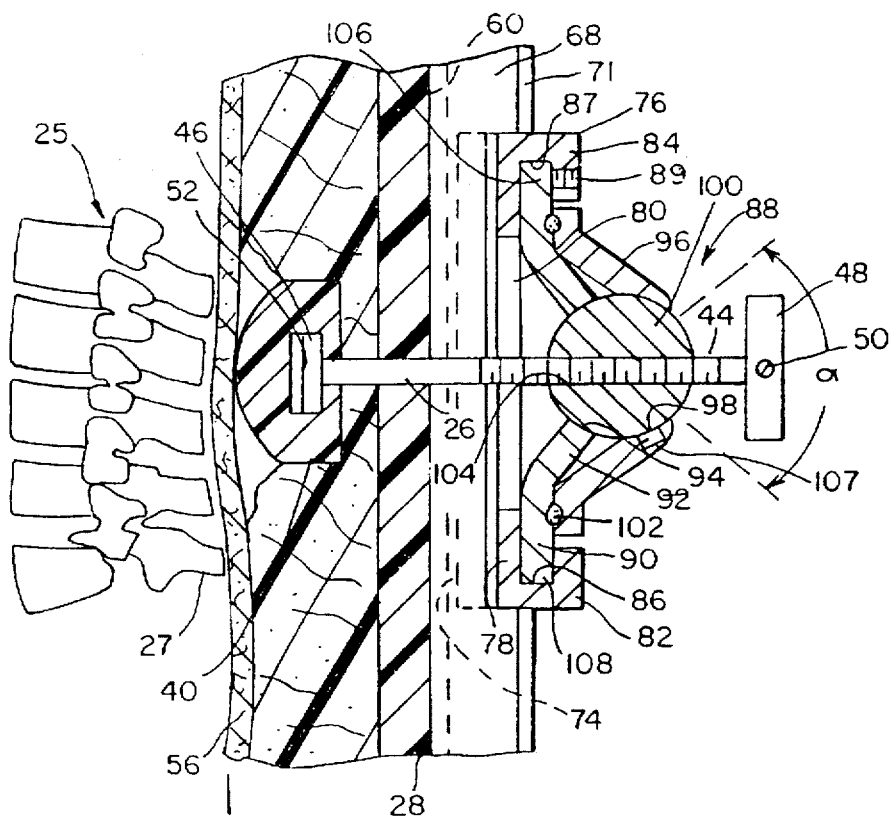
FIG. 4 is a cross-sectional view taken along line 4—4 of FIG. 3 in the direction of the arrows.
Figure 5:
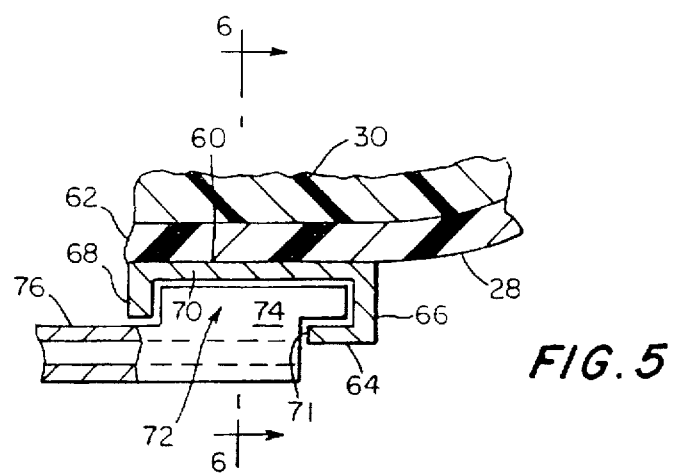
FIG. 5 is a cross-sectional view of one of the vertical rail means taken along line 5—5 of FIG. 3 in the direction of the arrows.
Figure 6:
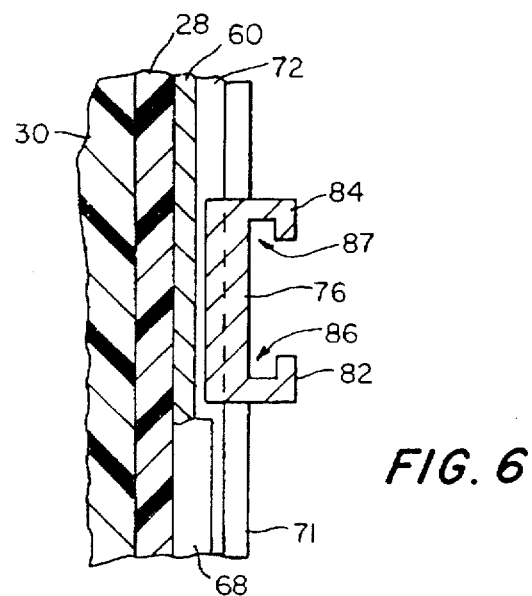
FIG. 6 is a cross-sectional view taken along line 6—6 of FIG. 5 in the direction of the arrows.

Referring to the embodiment of FIGS. 1 and 2, the pressure applicator means 24 preferably comprises an elongated thickened metal or plastic reinforcing segment or portion 32 of back section 14 which is provided with one or more rows such as 34, 36, 38 of threaded apertures 39 in which the thrust means 26 is adapted to be threadedly mounted such that it can be screwed inwardly to force its crown 40 against the spine area. These apertures are axially and laterally positioned with respect to the vertebra, e.g., of an average height person, such that the thrust means can apply forces to selected vertebra. In this regard, the apertures of rows 34 and 38 may be slanted inwardly toward the spinal axis such that the pressure can be directed, e.g., toward the transverse process rather than straight on, as against the spinous process.

The segment 32 preferably extends upwardly as portion 33 to adjacent the base of the skull such that pressure can be applied to cervical vertebra as well. This portion 33 is preferably curved concavely such that apertures 39 of rows 34 and 38 are directed inwardly, e.g., toward the superior articular facets of the cervical vertebra. In the use of this portion 33, a head strap such as 42 affixed to an extension such as 43 of portion 33 may be employed to maintain the head against said extension and keep at least an approximate axial alignment of the cervical spine as pressure is applied thereto.

The attachment means 20 may be of any convenient construction including strap and button, belt and buckle, grommet and button type snap fastener, zipper, and preferably cooperating Velcro loop and pile elements.

Figure 7:
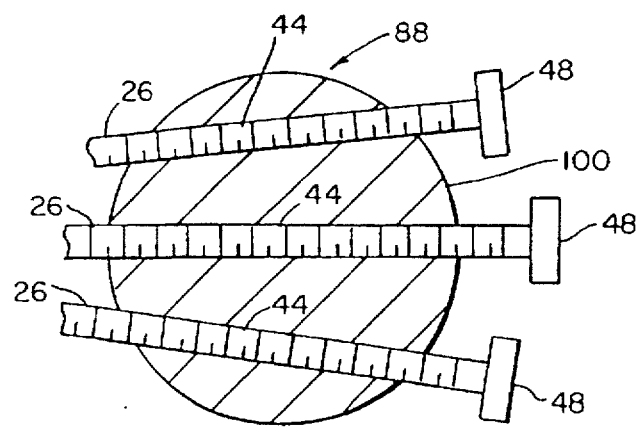
FIG. 7 is a view as in FIG. 4 of a variation of the plunger construction.

One preferred form of the thrust means 26 is shown in FIG. 7 and comprises a threaded shaft or screw 44 having a flanged inner end 46 and a handle means 48 preferably held onto the shaft by set screw 50 or equivalent structure. A rubber-like, fairly rigid crown 40 is provided rotatably on said inner end of the screw and is provided with a metal rub plate 52, preferably imbedded and non-rotatable in said crown and against which said inner end 46 can slide such that rotation of said shaft will not tend to rotate crown 40.

In the use of the embodiment of FIGS. 1, 2 and 7, a particular hole 39 location is selected for the thrust means and the shaft 44 thereof, with the handle 48 removed, is threaded thru the aperture to a point as shown in FIG. 7 where the semi-rigid crown 40 is forced into the softer cushion 30 and lies substantially in the plane 54 of the patients skin 56. The handle is then reattached to shaft 44. The vest sections are then latched together with sufficient force to snugly fit the patients body and thereby essentially fix the relative positions of the thrust means and the spinal portion against which pressure is to be exerted. The screw shaft 44 is then rotated to the desired extent to reposition the vertebra or a segment thereof.

It is particularly noted that two or more such thrust means can be employed at the same time such that, e.g., for a particular vertebra pressures can be applied not only to the area of the spinous process, but also to the area of either or both transverse processes, simultaneously.

Referring to the preferred embodiments of FIGS. 3–7, the back section 14 of the vest is provided as substantially two halves 56 and 58, the halves being separated by a gap or slot 59 and each half comprising the rigid or semi-rigid backing means 28 having the cushion means 30 affixed to the inside thereof, these halves each has and having a vertical rail means 60 which is preferably contoured to a patients spinal curvature, and affixed to its inner or spinal edge portion 62. Each rail means is formed with vertically extending wall sections 64, 66, 68 and 70 which provide a vertical slot generally designated 72. The term "vertical" as used throughout this application signifies the general posture attitude of the present device when worn by a patient in a standing position and is not intended to represent a mathematically precise orientation.

Slots 72 are dimensioned such that the end portions 74 of a slide plate generally designated 76 may be inserted therein, e.g., from the bottom of the rails 60, and the slide plate then slid upwardly to any desired vertical position between said rails. Said plate 76 is formed with a base 78 having a rectangular opening 80 therethrough and having wall segments 82 and 84 providing opposed grooves 86 and 87 respectively.

In this embodiment, the thrust means 26 has a universal type of mounting 88 which allows the thrust means, e.g., screw, to be pivoted in practically any direction, i.e., laterally, vertically, or diagonally, of course to a limited degree such as thru the angle such that the crown 40 can bear on the exact spinal area selected by the therapist or doctor.

Mounting 88 as shown is a preferred example only of useful structure and comprises a plate-like slide support 90 having a first segment 92 formed with a circular aperture 94, and a second segment 96 formed with a circular aperture 98. A generally ball shaped member 100 of e.g., metal or plastic is pivotally mounted between said segments which are welded together as at 102 after the ball has been so placed. The thrust shaft 44 is threaded through a bore 104 in the member 100 for screw movement toward and away from the spine. A set screw 107 of the like may be used to lock the ball in a desired position. The upper 106 and lower 108 edges of support 90 are dimensioned to slide in groove 86 in slide pate 76 formed by edge portions 87 to allow lateral adjustment positioning of the plunger means. One or more set-screws 89 or the like threaded into either or both of wall segments 82 and 84 may be used to fix the laterally adjusted position of support 90 with respect to the spine. As shown in FIG. 7, a more sophisticated mounting 88 is shown wherein multiple screws can be mounted at any desired angles relative to each other in multiple threaded apertures in member 100 for providing simultaneous pressures to adjacent areas of the spine.

In using the mounting structure of FIGS. 3–7, the two halves of the back section 14 of the vest are securely held together in the area where pressure is to be applied, by the interlocking structure of the end portions 74 of slide plate 76 and wall sections 64, 66, 68 and 70 of the vertical rail means 60. In order to ensure that all portions of the vest are maintained in snug contact with the patients body, any number of releasable latching means such as Velcro straps 110 or belts and buckles or the like affixable to both halves of back section 14 may be used below and above the slide plate to pull the halves toward each other after said slide plate is properly positioned. The slide plate may be releasably locked in vertical adjusted position by one or more set screws 112 or the like selectively placed in threaded apertures 114 in wall sections 64 of the vertical rails.

Figure 10:
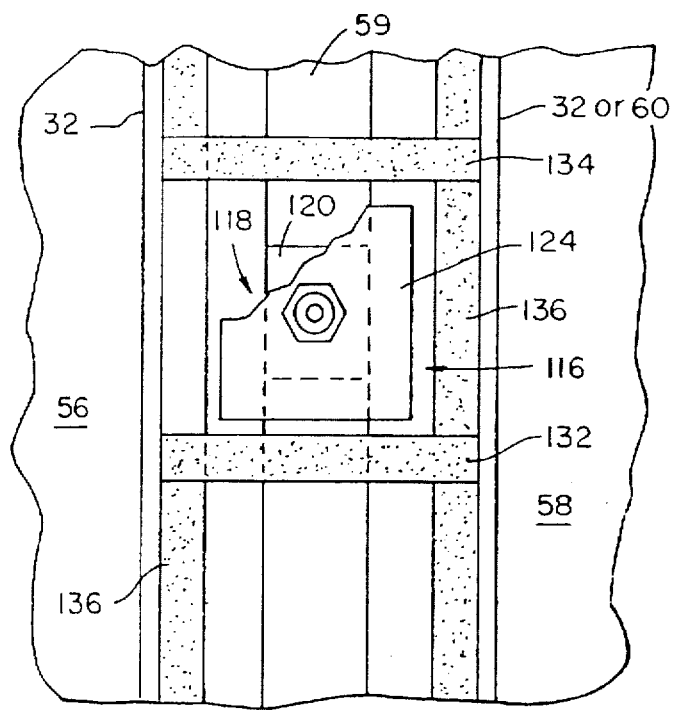
FIG. 10 is a rear view of the back section taken in the direction of line 10 in FIG. 9 with the torquing handle removed, and other portions broken away for clarity.
Figure 11:
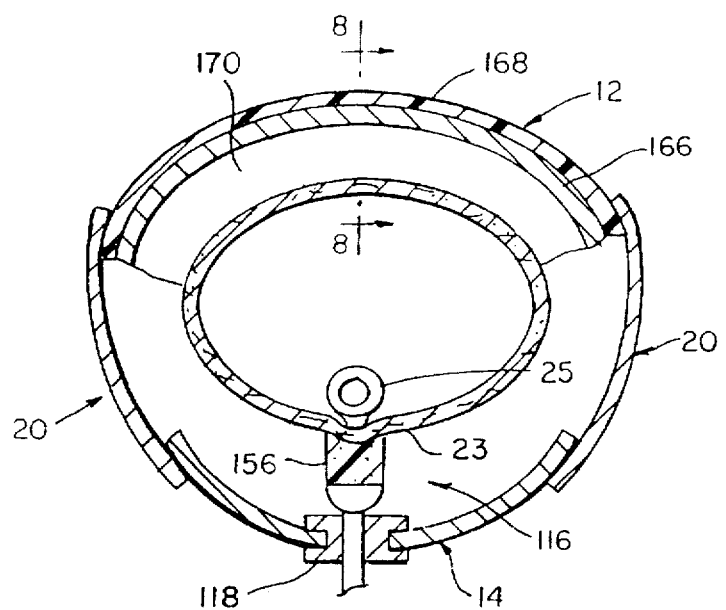
FIG. 11 is a lateral cross-section of a patients torso with the device of FIG. 9 in place.
Figure 16:
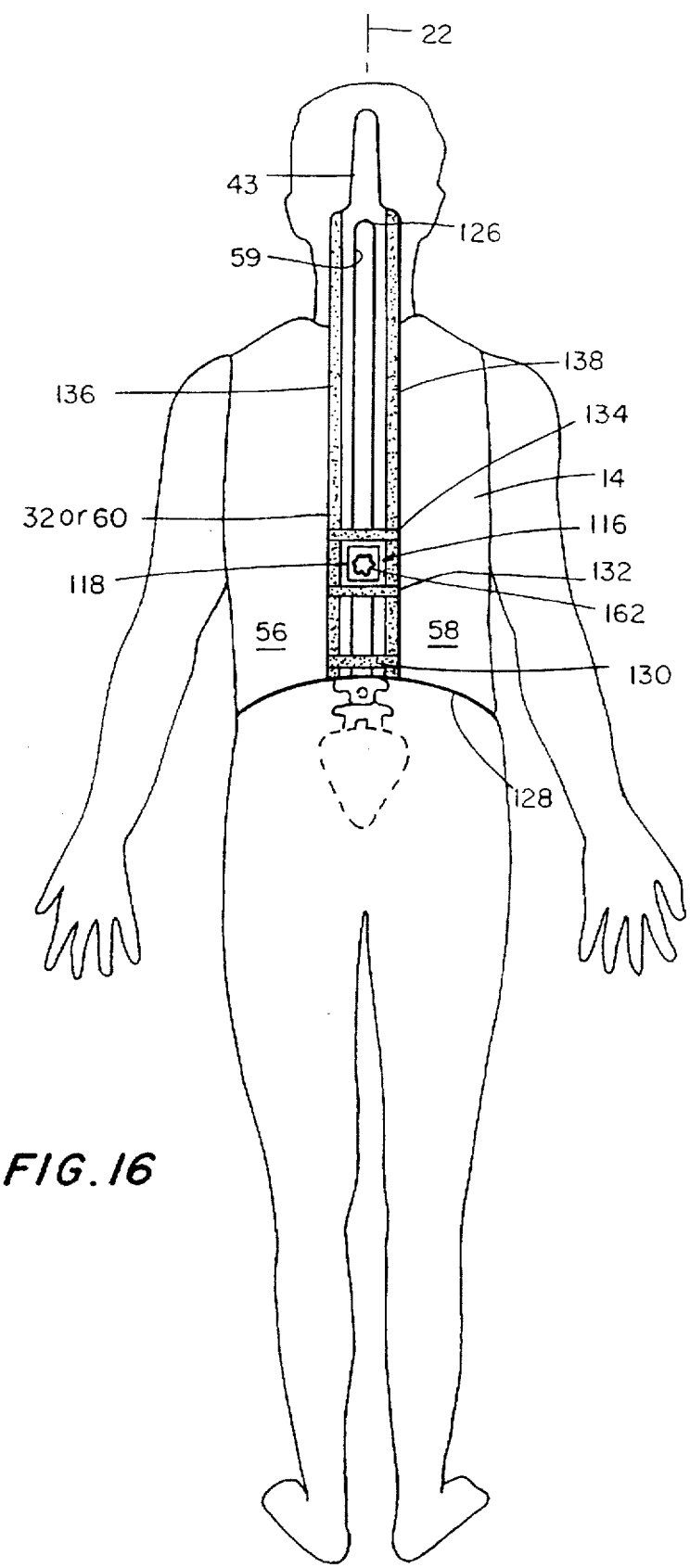
FIG. 16 is a view as in FIG. 2 but showing use of the sliding block thrust means of FIG. 12.

Referring to FIGS. 10–11, the thrust means 116 of the pressure applicator means comprises a sliding block means 118 having a generally rectangular core section 120 which is adapted to easily slidably fit into slot 59 between the two rail means 60 such that it can be positioned at any desired location along said slot. Block 118 is provided with inner and outer plate means 122, 124 respectively, which laterally stabilize 118 on said rail means 60. Block 118 is mounted in slot 59 in the manner described below with reference to FIG. 16 wherein the slot extends from point 126 at the upper portion of the rail means 60 (or slotted segment 32) thru the bottom edge 128 thereof. In assembling the block the connector means which tightly hold halves 56 and 58 laterally towards each other, such as lower Velcro straps 130 and 132, and if desired, also upper strap 134, are removed and the block slid up into slot 59 to a desired position, i.e., adjacent the vertebrae to be pressurized. The straps are then tightly reaffixed to the longitudinally extending Velcro mating straps 136, 138 such as to frictionally hold the blocks at said position within the slot. It is noted that by placing the straps or other connector means adjacent to the top and bottom of the outer plate 124, the positioned stability of the block 118 within slot 59 will be enhanced.

Figure 9:
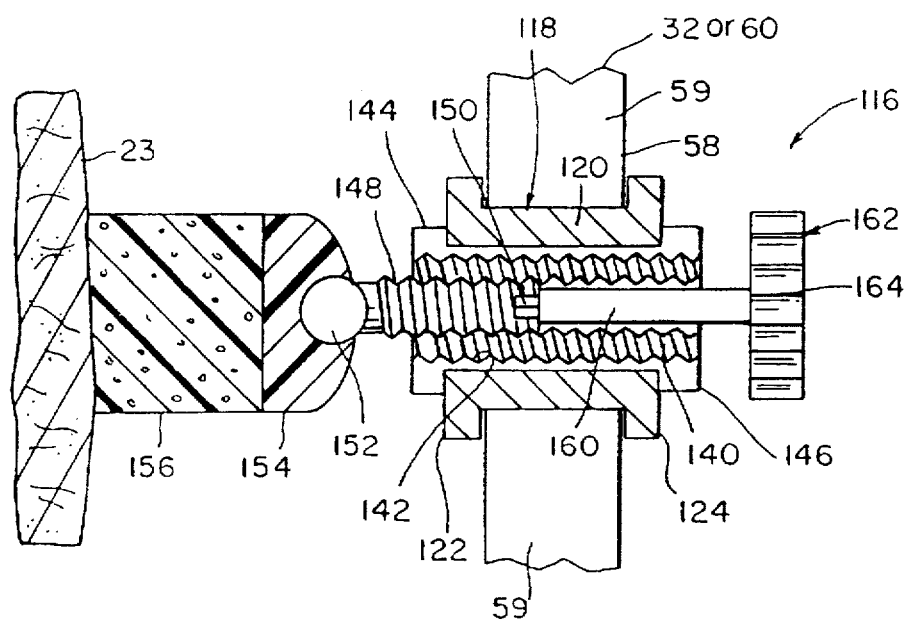
FIG. 9 is a cross-sectional view of the back section of a preferred embodiment of the vest taken along line 9—9 of FIG. 10 in the direction of the arrows and showing a rectangular sliding block.

Referring further to FIG. 9, one preferred form of the thrust means comprises an inner and outer threaded sleeve 140 which is screwed thru a threaded bore 142 in block 118 and is locked into position therein by nuts 144, 146. A screw member 148 is threaded into sleeve 140 and has a screw driver slot or Allen wrench socket, or other such shoulder means 150 provided in its inner end, and has a ball means 152 on its outer end. Ball 152 is mounted in a socket means 154 which is secured, e.g., by adhesive, to a cushion means 156 which may be dimensioned to simultaneously apply pressure to multiple vertebrae, and is constructed of material such as compressible elastomeric foam, e.g., foamed polyurethane, and which is adapted to bear against a patients skin or shirt back, or the like 158. This ball and socket construction is preferably dimensioned such that swiveling between the two requires at least some small degree of force, whereby positioning of cushion 156 with respect to a particular vertebrae can more easily be accomplished.

The particular tool 160 selected to engage shoulder 150 for screwing member 148 further in and forcing the cushion 156 harder against the patients back, or for screwing member 148 further out to relieve the pressure, is provided with torquing handle means, preferably round knob 162 having peripheral gripping indentations 164. Such construction allows the tool and handle to be removed after making the pressure adjustment, whereby improper adjustment by a non-professional cannot be made, and whereby the chance of inadvertent striking of the tool against something is eliminated. Alternatively, member 148 may be made sufficiently long to extend outwardly beyond plate 124 such as to be rotatable by any convenient means.

Figure 8:
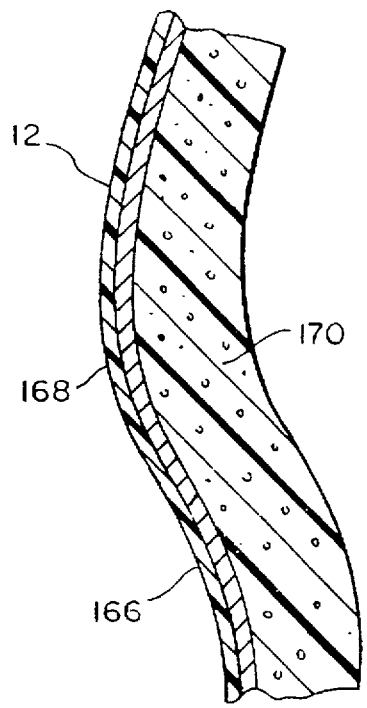
FIG. 8 is a cross-sectional view of the front section of a preferred embodiment of the vest taken along line 8—8 of FIG. 11 in the direction of the arrows.

Referring to FIGS. 8 and 11, front section 12 is preferably made of sheet aluminum 166 having a contour custom-formed to fit the patients frontal configuration and dimensions, and having an outer plastic, rubberized coating 168. A fairly thick foamed polyurethane or other cushion layer 170 is preferably affixed to the inner surface 172 of the aluminum sheet by adhesive or other means and, in concert with the custom-fitted contours of sheet 166 affords maximum comfort to the patient even though considerable pressure is being applied against his spine.

As best shown in FIG. 11, when substantial pressure is being exerted against a patients spine, back section 14 becomes spaced a substantial distance away from the patients back 23. This actually allows the professional attendant, chiropractor, orthopedist, or other to reach up in between the patients back 23 and the back section 14 to manipulate the cushion means 156 to fine tune the actual point of impingement thereof against the spine.

Referring to FIGS. 12–15, the thrust means comprises a round sliding block 123 equivalent in structure and function to block 118, but which may lend itself more readily to manufacture. Block 123 is provided with a bellows 125 or equivalent pneumatic device, sealed to inner plate 122 which plate is formed to provide an orifice 127 entering into the bellows and a check valve 129, the passage 131 of which becomes blocked by ball 133 when the pressure in the bellows is higher than the pressure in passage 131. This passage is kept open by conventional spider arms or projections 149 when the ball 133 is pressured away from its seat in passage 131. Hence the bellows is pressurized by any pressure generating means such as highly resilient bulb means 135 provided with a check valve 137 which acts oppositely to valve 129 such that squeezing the bulb will force its air contents into the bellows, and relaxing the bulb will refill it with air while valve 129 will retain the pressure in the bellows. A typical useful elongated of the bellows is, e.g., between about 1–2 inches, although smaller or larger bellows may be employed depending, e.g., on the patients size and therapeutic needs.

Figure 12:
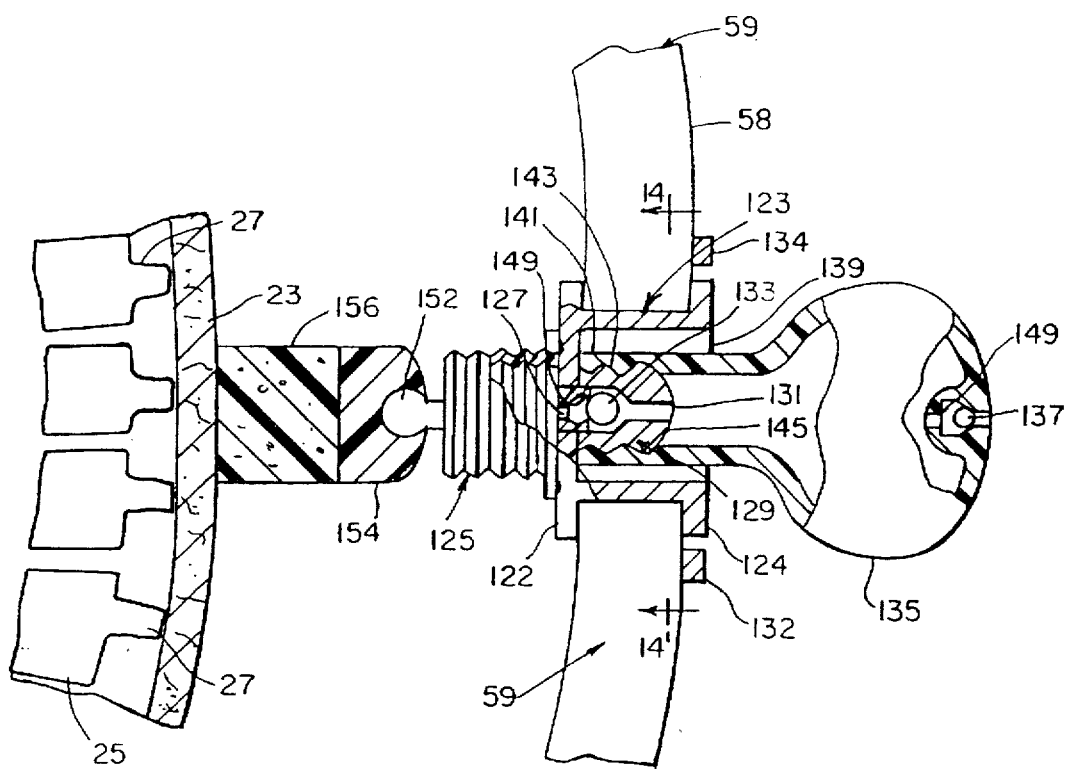
FIG. 12 is a cross-sectional view as in FIG. 9 showing the outline of the spine in schematic form, and showing another preferred embodiment of the invention using a circular sliding block and a bellows type of thrust device.
Figure 13:
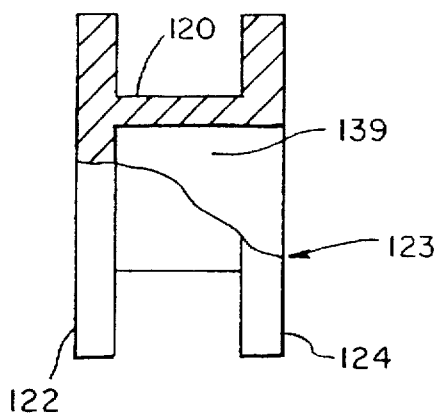
FIG. 13 is a partially sectioned isolated view of the sliding block of FIG. 12.
Figure 14:
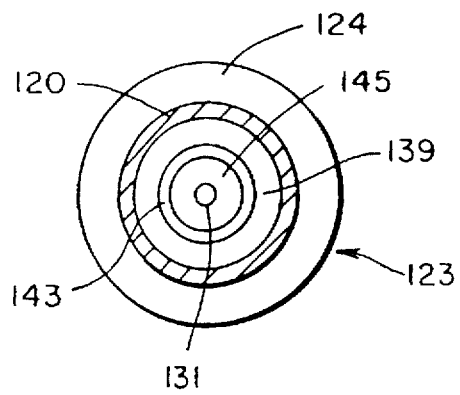
FIG. 14 is a cross-sectional view taken along line 14—14 of FIG. 12 with the pressurizing bulb removed and the back section of the vest means not shown.
Figure 15:
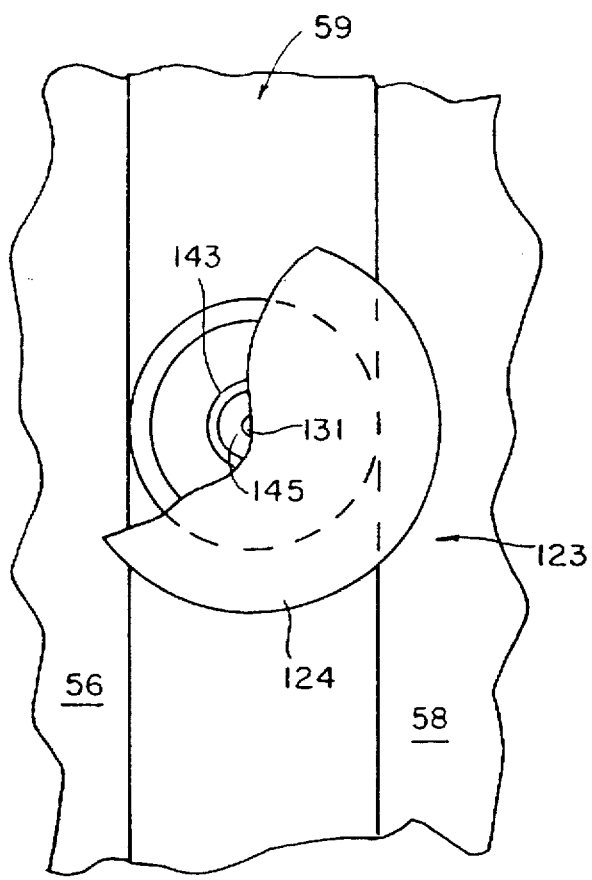
FIG. 15 is a view as in FIG. 14 with portions broken away and with portions of the back section and slot shown.

A convenient structure for this embodiment of the thrust means is as shown in FIG. 12 wherein plate 124 is provided with a wide aperture at 139 such that the stem 141 of the bulb means may be sealingly shoved over the peripheral sealing ridges 143 of the body 145 of check valve 129. Likewise, the stem and bulb may easily removed after the bellows is pressurized. It is noted that the bellows may be provided with a bicycle type of pressuring valve extending into aperture 132 for use with a conventional bicycle pump.

In another preferred embodiment, the thrust means 116 such as block means 118 or equivalent may be cast directly into a plaster body cast in an emergency situation in a hospital or other facility. Such is the equivalent of the structure shown in FIG. 9 wherein the element 32 or 60 comprises the plaster cast. In this embodiment, the need for sliding block 118 in slot 59 usually would not be present, and 32 or 60 could be a solid cast which locks block 118 in a single position.

The invention has been described in detail with particular reference to preferred embodiments thereof, but it will be understood that variations and modifications will be effected with the spirit and scope of the invention.

I claim:

1. A device for applying external pressure to one or more of a patients vertebra for repositioning the same and/or maintaining the position thereof in the patients spine, or for forcing and maintaining segments of a broken vertebra in healing contact with each other, said spine lying generally along a spinal axis, said device comprising an upper body vest means adapted to substantially surround the upper body of a patient from adjacent the waist to adjacent the neck in a snug manner, said vest means having front and back sections provided with cooperating segments of attachment means for clamping said sections to each other to snugly surround said upper body, said back section having an elongated substantially rigid portion extending substantially the length of said back section and formed to closely conform to the curvature of the patients spine and lie adjacent thereto, one element of a pressure applicator means provided on said elongated portion, thrust means providing another element of said applicator means and being mounted on said one element for controlled, reciprocable movement in a direction generally normal to said spinal axis for applying external pressure in a controlled manner to a selected portion of said spine.

2. The device of claim 1 wherein mounting means is provided for said thrust means for allowing a universal type motion thereof whereby pressure can be directed in a wide range of angles against selected portions of the spine.

3. The device of claim 2 wherein said mounting means comprises a generally ball shaped member mounted in a socket shaped base wherein said thrust means is threadedly mounted thru said member and said member is pivotal within said base affixed to said elongated portion for adjusting the angle of said thrust means in a generally universal manner relative to the spine.

4. The device of claim 3 wherein said mounting means is provided on a slide support having upper and lower edge portions mounted on slide plate means for generally laterally directed adjustment motion with respect to said spinal axis, and wherein side edge portions of said slide plate means are mounted for vertical adjustment motion in vertical slots provided on rail means, whereby the pressure applied by said thrust means can be directed in a wide range of angles to the spine at essentially any vertical location along the spine.

5. The device of claim 3 wherein multiple thrust means are mounted in said ball shaped member.

6. The device of claim 1 wherein said vest means are custom formed to fit snugly a particular patients body.

7. The device of claim 1 wherein said cooperating segments of said attachment means comprises quick release hook and loop segments.

8. The device of claim 1 wherein said pressure applicator means comprises at least one row of vertically spaced threaded apertures in which apertures one or more said thrust means can be selectively threaded.

9. The device of claim 1 wherein the inner surfaces of said vest means sections are provided with cushion means affixed thereto for cushioning said upper body against the reactive forces generated by pressure developed by operation of said applicator means.

10. The device of claim 1 wherein said thrust means comprises a device which is expansible by pressurizing fluid contained therein.

11. The device of claim 10 wherein said device comprises a slidable block means slidable in a slot in said elongated portion and having a bellows which can expand lengthwise a distance of about 1-2 inches in response to air or hydraulic fluid being pressurized therein, and supporting a cushion means for engaging a patients back.

12. The device of claim 1 wherein said thrust means comprises a slidable block means slidable in a slot in said elongated portion and having a screw means threadedly mounted therethrough and supporting a cushion means for engaging a patients back.

* * * * *